(12) United States Patent
Takakura et al.

(10) Patent No.: US 7,875,264 B2
(45) Date of Patent: Jan. 25, 2011

(54) SELF-TANNING COSMETIC

(75) Inventors: Yoshihito Takakura, Yokohama (JP); Tetsuya Kanemaru, Yokohama (JP); Seiji Sano, Yokohama (JP); Fumiaki Matsuzaki, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 425 days.

(21) Appl. No.: 11/920,325

(22) PCT Filed: Aug. 5, 2005

(86) PCT No.: PCT/JP2005/014417

§ 371 (c)(1),
(2), (4) Date: Nov. 13, 2007

(87) PCT Pub. No.: WO2007/017921

PCT Pub. Date: Feb. 15, 2007

(65) Prior Publication Data

US 2009/0098068 A1    Apr. 16, 2009

(51) Int. Cl.
*A61K 8/06* (2006.01)
*A61K 8/19* (2006.01)
*A61K 8/35* (2006.01)
*A61K 33/26* (2006.01)
*A61Q 17/04* (2006.01)

(52) U.S. Cl. .................. 424/59; 424/646; 514/938; 514/975

(58) Field of Classification Search .................. None
See application file for complete search history.

(56) References Cited

U.S. PATENT DOCUMENTS

| | | | | |
|---|---|---|---|---|
| 5,879,667 A | * | 3/1999 | Hanna et al. | 424/70.7 |
| 6,086,688 A | * | 7/2000 | Doutre et al. | 148/437 |
| 7,357,919 B2 | * | 4/2008 | Candau | 424/59 |
| 2004/0253197 A1 | * | 12/2004 | Sakuta | 424/70.12 |
| 2005/0118121 A1 | * | 6/2005 | Kuroda | 424/63 |

FOREIGN PATENT DOCUMENTS

| | | | |
|---|---|---|---|
| EP | 1473026 A1 | | 11/2004 |
| EP | 1477159 A | | 11/2004 |
| JP | 60-226805 A | | 11/1985 |
| JP | 2002338448 A | * | 11/2002 |
| WO | WO 94/15580 A | | 7/1994 |
| WO | WO 2005/004826 A | | 1/2005 |

* cited by examiner

*Primary Examiner*—Johann R Richter
*Assistant Examiner*—Frank I Choi
(74) *Attorney, Agent, or Firm*—Townsend & Banta

(57) ABSTRACT

The present invention provides a self tanning cosmetic containing 0.2-20.0 mass % of dihydroxyacetone and 0.1-10.0 mass % of an inorganic pigment powder whose surface is treated with silica coating followed by a hydrophobing treatment.

The present invention provides a cosmetic that has superior storage stability, is free of discoloration and odor generation, and achieves both the decorative effect of the pigment immediately following application and the long term dyeing effect of dihydroxyacetone.

8 Claims, No Drawings

SELF-TANNING COSMETIC

TECHNICAL FIELD

The present invention relates to a self tanning cosmetic. More specifically, it relates to a self tanning cosmetic that has instantaneous and sustained coloring effects as well as superior storage stability.

BACKGROUND ART

A self tanning cosmetic is a cosmetic that colors the skin. The coloring effect of a dye usually starts several hours after application, peaks in one to two days, and decays until the skin color returns to the original after one week.

A self tanning cosmetic is a cosmetic that provides the appearance of natural and healthy sun-tanned skin without exposure to harmful ultraviolet light. A self tanning cosmetic that contains a dye called dihydroxyacetone is known as having a sustained coloring effect (Patent Documents 1-5).

On the other hand, makeup cosmetics such as foundation containing a pigment have been proposed as a method to instantaneously provide suntan color skin. A tint type self tanning cosmetic containing a pigment have been proposed as having sustained and also instantaneous effects (Patent Document 6).

Patent Document 1: Japanese Patent Laid-Open H7-101843 bulletin
Patent Document 2: Japanese Patent Laid-Open H7-101848 bulletin
Patent Document 3: Japanese Patent Laid-Open 2001-213747 bulletin
Patent Document 4: Japanese Patent Laid-Open 2002-338448 bulletin
Patent Document 5: Japanese Patent Laid-Open 2005-145860 bulletin
Patent Document 6: Japanese Patent Laid-Open 2003-113065 bulletin

DISCLOSURE OF INVENTION

Problem that the Present Invention Aims to Solve

However, dihydroxyacetone that is contained in a self tanning cosmetic has a problem in that it decomposes over days and thus the color tone changes and an offensive odor emerges. In particular, it becomes extremely unstable when coloring agents such as inorganic pigments are added, and as a result manufacturing a stable tint type self tanning cosmetic was very difficult.

In view of the aforementioned problem, the inventors conducted earnest research and discovered that instability of dihydroxyacetone is prevented and a self tanning cosmetic having very superior storage stability can be provided by adding powder prepared by coating the surface of an inorganic pigment powder with silica and hydrophobing [the powder] to a self tanning cosmetic containing dihydroxyacetone, thus completing the present invention.

The object of the present invention is to provide a cosmetic that has superior storage stability and achieves both the decorative effect of the pigment immediately following application and the dyeing effect of dihydroxyacetone that is sustained for a long time.

Means to Solve the Problem

That is, the present invention provides a self tanning cosmetic containing 0.2-20.0 mass % of dihydroxyacetone and 0.1-10.0 mass % of an inorganic pigment powder whose surface is treated with a silica coating followed by a hydrophobing treatment.

Also, the present invention provides the aforementioned self tanning cosmetic wherein said inorganic pigment powder is iron oxide.

Furthermore, the present invention provides the aforementioned self tanning cosmetic wherein said hydrophobing treatment uses octyltriethoxysilane.

Also, the present invention provides the aforementioned self tanning cosmetic wherein said inorganic pigment powder is iron oxide.

In addition, the present invention provides the aforementioned self tanning cosmetic wherein polyether-modified silicone is used for the emulsifier.

Also, the present invention provides the aforementioned self tanning cosmetic wherein branched polyether-modified silicone and cross-linked polyether-modified silicone are used for the emulsifier.

EFFECTS OF THE INVENTION (1) The self tanning cosmetic of the present invention prevents the instability of dihydroxyacetone caused by inorganic pigments. It is a self tanning cosmetic with excellent storage stability.
(2) The self tanning cosmetic of the present invention is a tint type self tanning cosmetic that has both sustained and instantaneous effects. That is, both the instantaneous coloring effect (decorative effect) of the inorganic pigment and the long term dyeing effect of dihydroxyacetone are achieved at the same time.
(3) Since it has a decorative effect by means of the inorganic pigment, it can also be used as a makeup cosmetic. Since a large amount of an inorganic pigment can be added in a stable manner, any makeup cosmetic can be designed. Also, since the pigment is hydrophobed, it does not come off easily from the skin, resulting in a makeup cosmetic with a lasting cosmetic effect.
(4) When the formulation is a water-in-oil type emulsified composition, a water-in-oil type self tanning cosmetic with an excellent sensation during use can be provided.

BEST MODE FOR CARRYING OUT THE INVENTION

Dihydroxyacetone

The dihydroxyacetone used in the present invention, abbreviated as DHA, is a prior art cosmetic material (skin dye) commonly used in self tanning cosmetics. Its content in the self tanning cosmetic is required to be 0.2-20.0 mass %, preferably 1.0-15.0 mass %, of the total amount of the self tanning cosmetic. If the content is less than 0.2 mass %, then the self tanning effect cannot be obtained. If it is over 20.0 mass %, then the storage stability is degraded.

The purity of dihydroxyacetone used in the present invention is preferably 90.0 mass % or higher, more preferably 95.0 mass % or higher, and even more preferably 97.0 mass % or higher.

[Hydrophobed Silica-coated Inorganic Pigment Powder]

The inorganic pigment powder used in the present invention is a powder obtained by using a prior art method to coat the surface of an inorganic pigment powder with silica, followed by a hydrophobing treatment.

The inorganic pigment powder content in the self tanning cosmetic is required to be 0.1-10.0 mass %, preferably 0.5-7.0 mass %. When the content is less than 0.1 mass %, then the instantaneous coloring effect is poor and the decorative effect of the skin is lost. If it is over 10.0 mass %, then adequate dispersion in the cosmetic becomes difficult and the storage stability is degraded.

Selection of said inorganic pigment is not limited as long as it is an inorganic pigment commonly used in makeup cosmetics; examples include sericite, mica, titanium oxide, talc, kaolin, and iron oxide. These can be used either independently or in combinations of two or more.

In terms of the stability and the decorative effect, particularly preferable inorganic pigments are iron oxide (black), iron oxide (yellow), and iron oxide (red). In the present invention, iron oxide (black), iron oxide (yellow), and iron oxide (red) can preferably be used either independently (only one kind is added) or in combinations (two or three kinds are added).

Selection of the silica treatment method to coat the surface of the inorganic pigment is not limited in particular; a prior art treatment method can be used. Examples include a method in which an inorganic pigment is dispersed in an aqueous solution of sodium silicate, followed by neutralization with acid (Japanese Patent Laid-Open S60-226805 bulletin), a method in which an inorganic pigment is dispersed in an aqueous solution of silicate that is neutralized with acid in advance (WO98/26011), and a method in which a silica coating is formed by using a hydrolyzing organosilicon compound such as tetraethoxysilane (Pat. 3,570,730). The amount of the silica coating varies depending on the type of the inorganic pigment; it is about 1-30 mass %, preferably 2-20 mass %. If the silica coating is less than 1 mass % then the amount of silica is not sufficient and the coating effect on the entire surface of the inorganic pigment is hard to obtain. If it is over 30 mass % and if the inorganic pigment is a coloring pigment, then the coloring ability may weaken due to a reduction in the pigment concentration.

The silica-coated inorganic pigment powder further receives a hydrophobing treatment on its surface. Selection of the hydrophobing treatment method is not limited in particular; a prior art method is used for the treatment. Examples include a treatment in which silicones such as methylhydrogen polysiloxane, methylhydrogen polysiloxane/dimethyl polysiloxane copolymer, and dimethyl polysiloxane are used, a treatment in which silane compounds such as octyltriethoxysilane and hexyltrimethoxysilane are used, a treatment in which a fatty acid such as palmitic acid or stearic acid is used, a metal soap treatment in which an alkali metal salt or alkali earth metal salt of said fatty acid is used, and a fluorine treatment in which diethanolamine perfluoroalkylphosphate, perfluoroalkyltrimethoxysilane, etc. are used. In the present invention, silica-coated inorganic pigment powder treated with octyltriethoxysilane is particularly preferable.

The self tanning cosmetic of the present invention is prepared by adding the aforementioned essential ingredients to a conventional cosmetic base agent. Other ingredients can be added to the self tanning cosmetic of the present invention within a range that does not degrade the effect of the present invention. For example, powder ingredients, liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, ultraviolet absorbents, sequestering agents, lower alcohols, polyhydric alcohols, sugars, amino acids, organic amines, polymer emulsions, pH adjusting agents, skin nutrients, vitamins, antioxidants, antioxidation assistants, perfumes, water, etc. can be blended in as necessary to prepare [the self tanning cosmetic] according to the target formulation with a conventional method.

"Preferable Formulation: Water-in-oil Type Emulsified Composition"

The formulation of the self tanning cosmetic of the present invention is not limited in particular; in terms of the sensation during use and stability, a water-in-oil type emulsified composition is preferable. The aforementioned inorganic pigment powder is preferably dispersed in the oil phase. A desired amount of the inorganic pigment powder can be added in a stable manner by dispersing it in the oil phase. As a result, a makeup type self tanning cosmetic having superior instantaneous coloring effect (decorative effect) can be provided.

For a self tanning cosmetic that is a water-in-oil type emulsified composition, selection of the oil component that constitutes the oil phase in which the inorganic pigment powder is dispersed is not limited in particular. For example, the following oil components can be used. The oil phase is usually 10-60 mass %, preferably 20-40 mass %, of the total amount of the self tanning cosmetic. In addition to the following oil components, oil soluble ingredients such as drugs can be blended into the oil phase.

(1) Examples of the liquid fats and oils include avocado oil, tsubaki oil, turtle fatty acid, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice bran oil, Chinese gimlet oil, Japan gimlet oil, jojoba oil, germ oil, and triglycerin.

(2) Examples of the solid fats and oils include cacao butter, coconut oil, hydrogenated coconut oil, palm oil, palm kernel oil, Japanese core wax nucleus oil, hydrogenated oil, Japanese core wax, and hydrogenated castor oil.

(3) Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, POE hydrogenated lanolin ethyl alcohol ether, ceresin, and microcrystalline wax.

(4) Examples of the hydrocarbon oils include liquid petrolatum, ozocerite, squalane, pristane, paraffin, squalene, and petrolatum.

(5) Examples of the higher fatty acids include lauric acid, myristic acid, palmitic acid, stearic acid, behenic acid, oleic acid, undecylenic acid, isostearic acid, linolic acid, linoleic acid, eicosapentaenoic acid (EPA), and docosahexaenoic acid (DHA).

(6) Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain ethyl alcohols (for example, mono stearyl glycerin ether (batyl alcohol), 2-decyltetradecynol, lanolin alcohol, cholesterol, phytosterol, hexyl dodecanol, iso stearyl alcohol, and octyl dodecanol).

(7) Examples of the ester oils include isopropyl myristate, cetyl octanoate, octyl dodecyl myristate, isopropyl palmitate, butyl stearate, hexyl laurate, myristil myristate, decyl oleate, dimethyl hexyl decyl octanoate, cetyl lactate, myristil lactate, lanolin acetate, iso cetyl stearate, iso cetyl isostearate, cholesteryl hydroxy 12-stearate, ethylene glycol di-2-ethylhexanoate, dipentaerythritol fatty acid ester, n-alkylene glycol monoisostearate, neopentyl glycol dicaprate, diisostearyl malate, glyceryl di-2-heptylundecanoate, trimethylolpropane tri-2-ethylhexanoate, trimethylolpropane triisostearate, tetra-2-pentaerythritol ethylhexanoate, glycerin tri-2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, methyl castor oil fatty acid, oleyl oleate, aceto glyceride, 2-heptyl undecyl palmitate, diisobutyl adipate, 2-octyldodecyl N-lauroyl-L-glutamate, di-2-heptyl undecyl adipate, ethyl laurate, di-2-ethylhexyl sebacate, 2-hexyl decyl myristate, 2-hexyldecyl palmitate, 2-hexyl decyl adipate, diisopropyl sebacate, 2-ethylhexyl succinate, and triethyl citrate.

(8) Examples of the silicone oils include chain polysiloxanes (for example, dimethylpolysiloxane, methylphenyl polysiloxane, and diphenyl polysiloxane); ring polysiloxanes (for example, octamethylcyclotetrasiloxane, decamethyl cyclopenta siloxane, and dodecamethyl cyclohexa siloxane), silicone resins forming a three-dimensional network structure, silicone rubbers, and various modified polysiloxanes (amino-modified polysiloxane, polyether-modified polysiloxane, alkyl-modified polysiloxane, and fluorine-modified polysiloxane).

Selection of the emulsifier to be used is not limited; polyether-modified silicone is preferable. In particular, branched polyether-modified silicone and cross-linked polyether-modified silicone are preferably used.

The polyether-modified silicone content is required to be 0.1-10.0 mass %, preferably 0.5-5.0 mass %, of the total amount of the self tanning cosmetic. If the content is less than 0.1 mass %, then the stability of the emulsion is impaired. If it is over 10.0 mass %, then stickiness at the time of application increases and the desirable texture as a cosmetic is impaired.

The branched polyether-modified silicone and the cross-linked polyether-modified silicone can be used independently or in combination within the aforementioned content range. It is particularly preferable to use them in combination since this way more stable water-in-oil type emulsified compositions can be obtained and the dihydroxyacetone can be stabilized more.

Selection of said polyether-modified silicone is not limited. For example, ethoxy adducts of alkylpolysiloxane having an alkyl chain with 20 or less carbon atoms (such as cetyl dimethyl silicone copolyol and dimethyl silicone copolyol), ethoxy adducts of phenylpolysiloxane having a phenyl group, as well as compounds prepared by esterifying the ethoxy end of these with a carboxylic acid having 18 carbon atoms or less (such as dimethyl silicone copolyol isostearate, dimethyl silicone copolyol stearate and dimethyl silicone copolyol laurate). Branched polyether-modified silicone that is the aforementioned polyether-modified silicone whose main chain is branched is preferable.

Of these, straight chain and branched dimethyl silicone copolyol is preferable in terms of ease of stabilizing the dihydroxyacetone; particularly preferable is branched dimethyl silicone copolyol.

The polyether-modified silicones can be used independently or in combination of two or more types.

Preferable commercially available products include KSG210 as the cross-linked type, KF6028 and KF6038 as the branched type, and KF6016 and KF6107 as the straight chain type (all from Shin-Etsu Chemical Co., Ltd.)

The cross-linked polyether-modified silicone used in the present invention is a prior art emulsifier. For example, out of combinations of organo hydrogen polysiloxane represented by general formula $R^1_a R^2_b H_c SiO_{(4-a-b-c)/2}$ (I) and/or $R^1_j H_k SiO_{(4-j-k)/2}$ (II) and polyoxyalkylene represented by general formula $C_m H_{2m-1} O(C_2 H_4 O)_p (C_3 H_6 O)_q C_m H_{2m-1}$ (A) and/or organo polysiloxane represented by general formula $R^1_d R^3_e SiO_{(4-d-e)/2}$ (B), an ingredient represented by said general formula (I) and/or said general formula (A) can be used as an essential ingredient to perform addition condensation to obtain a silicone polymer.

In the aforementioned general formulas, each of $R^1$s denotes the same or different group chosen from a univalent alkyl group, aryl group, aralkyl group or halogenated hydrocarbon having 1-30 carbon atoms, $R^2$ denotes an organic group represented by the general formula $-C_n H_{2n} O(C_2 H_4 O)_f (C_3 H_6 O)_g R^4$, $R^3$ denotes a univalent hydrocarbon group having an end vinyl group and 2-10 carbon atoms, $R^4$ denotes a hydrogen atom or a saturated organic group having 1-10 carbon atoms or a group represented by $R^5-(CO)-$, and $R^5$ denotes a saturated organic group having 1-5 carbon atoms. For a, b, c, d, e, j, and k, $1.0 \leq a \leq 2.5$, $0.001 \leq b \leq 1.0$, $0.0011 \leq c \leq 1.0$, $1.0 \leq d \leq 3.0$, $0.001 \leq e \leq 1.5$, $1.0 \leq j \leq 3.0$, and $0.01 \leq k \leq 1.5$.

f and p are integers 2-200, g and q are integers 0-200, f+g is 3-200, p+q is 3-200, and m and n are 2-6.

A preferable commercially available product is KSG210 (from Shin-Etsu Chemical Co., Ltd.).

<A Method of Preparing a Water-in-oil Type Self Tanning Cosmetic>

The water-in-oil type self tanning cosmetic of the present invention is preferably prepared with the following method because it gives a cosmetic with superior storage stability over time.

(1) Dihydroxyacetone is dissolved in water (preferably containing ethanol and polyol) to obtain the water phase consisting of an aqueous solution containing dihydroxyacetone (water phase).

(2) The oil phase that contains the emulsifier (it is preferable to use both the branched polyether-modified silicone and cross-linked polyether-modified silicone) and the inorganic pigment powder is obtained (oil phase).

(3) The dihydroxyacetone-containing aqueous solution (water phase) is added to the oil phase as stirring is carried out.

The stirring speed is preferably 150 rpm or higher, more preferably 300 rpm or higher. If said stirring speed is 150 rpm or higher, then a cosmetic with superior stability of dihydroxyacetone is provided.

The liquid temperature during the stirring is preferably 15-50° C., more preferably 20-45° C. If said liquid temperature during the stirring is within the indicated range, then a cosmetic with superior stability of dihydroxyacetone is provided.

For stirring, a common emulsifying device such as a paddle mixer, homomixer, or disper is preferably used.

The self tanning cosmetic of the present invention is preferably a W/O type (water-in-oil) emulsion prepared as described above. In such an emulsion, dihydroxyacetone is incorporated into the polyol that forms the dispersing element and stabilized, which results in a cosmetic that is superior in terms of long term storage stability and free of color tone changes and odor generation.

The average particle size of the polyol that forms the dispersing element is preferably 1-5 micrometers, more preferably 1-3 micrometers. An embodiment that is a P/S type (polyol-in-silicone) emulsion is also preferable.

The mass ratio of the oil phase and the water phase (oil phase/water phase) is preferably oil phase/water phase=6/4-

1/9, more preferably 4/6-2/8, and even more preferably about 3/7. Outside of this range, the stability of the cosmetic may become poor.

Dihydroxyacetone, i.e. the dye, is dissolved in the water phase. Water is a constituent of the water phase. The water content is usually 30-95 mass %, preferably 50-85 mass %, of the total amount of the water-in-oil type self tanning cosmetic.

Ethanol can be blended into the water phase. It is also preferable to blend in, as a humectant, polyhydric alcohols such as glycerin and sorbitol, polysaccharides such as hyaluronic acid, amino acids such as pyrrolidone carboxylic acid, as well as other water soluble ingredients.

<Preferable Product Form>

The self tanning cosmetic of the present invention can be used as a makeup cosmetic such as a cream foundation having a self tanning effect.

Also, it can be used in the same way as a common self tanning cosmetic is used if it is washed away right after application.

In particular, a preferable cream-like foundation can be prepared by blending 1-5 mass % of an emulsifier (branched polyether-modified silicone and cross-linked polyether-modified silicone), 50-85 mass % of water, 3-10 mass % of dihydroxyacetone, 15-20 mass % of the oil component, 1-10 mass % of polyol, and 1-5 mass % of iron oxide whose surface is coated with silica and also hydrophobed with octyltriethoxysilane.

EXAMPLES

The present invention is described in detail below by referring to Examples. The present invention is not limited to these examples. The blend ratios are in mass-percentage units unless specified otherwise.

Using the recipes shown in Tables 1-4, a conventional method was used to prepare water-in-oil type self tanning cosmetics, which were investigated for the following effects.

The results indicate that the self tanning cosmetic of each Example has excellent storage stability (appearance, odor, and viscosity). In particular, the high temperature stability in the system in which dihydroxyacetone and the inorganic pigment are blended is a significant effect that cannot be predicted. Also, the instantaneous coloring effect (decorative effect) and the long term coloring effect were both shown to manifest at the same time. Also, the water-in-oil type emulsified self tanning cosmetic of each Example gives an excellent sensation during use.

(Preparation Method)

A solution in which the water phase ingredients were homogeneously dissolved was added to the oil phase in which the inorganic pigment was homogeneously dispersed, as stirring was carried out.

<Evaluation of Appearance and Odor Stability>

Each cosmetic was kept in thermostatic baths at temperatures −20° C., −5° C., room temperature (25° C.), 37° C., and 50° C.; after one month the stability in terms of appearance and odor was comprehensively evaluated using the following evaluation criteria based on visual observation of the color tone and whether or not odor was generated.

<Evaluation Criteria>

No change in color tone, no odor generation ○
Some color tone change and/or odor generation Δ
Very significant color tone change and/or odor generation X <Evaluation of Viscosity Stability>

Each cosmetic was kept in thermostatic baths at temperatures −20° C., −5° C., room temperature (25° C.), 37° C., and 50° C.; after one month the stability in terms of viscosity was evaluated using the following evaluation criteria.

<Evaluation Criteria>

No significant change from the freshly prepared state ○
Only at 50° C., a significant reduction in viscosity is observed compared with the freshly prepared state Δ
At room temperature to 50° C., a significant reduction in viscosity is observed compared with the freshly prepared state X <Evaluation of the Decorative Effect on the Skin>

Each cosmetic was applied on a face and the decorative effect of the coloring agent on the skin immediately following the application (instantaneous coloring effect) was visually evaluated using the following evaluation criteria.

<Evaluation Criteria>

The skin color changed significantly, giving the appearance of suntanned skin. ○
A change in the skin color is observed at the time of application but after thorough rubbing-in no difference is observed between before and after application. Δ
No change in the skin color is observed either at the time of application or immediately following application. X <Evaluation of the Sustained Dyeing Effect>

18 microliters of the cosmetic was applied on a 3×3 cm² area on the forearms of six test subjects and washed off after two hours; the sustained dyeing effect (long term coloring effect) was evaluated after six days by using the following evaluation criteria.

<Evaluation Criteria>

The dyeing effect is sustained to the degree where the application site is perfectly recognizable. ○
The application site is largely recognizable, but the boundary of the dyed site is not recognizable. Δ
The skin color is completely back to the original color and the application site is not recognizable. X

TABLE 1

| Classification | | Raw material | Example 1 | Example 2 | Example 3 |
| --- | --- | --- | --- | --- | --- |
| Water phase | Water | Ion-exchanged water | 58.08 | 56.58 | 56.33 |
| | Alcohol | Ethyl alcohol | 5 | 5 | 5 |
| | Humectant | Dipropylene glycol | 3 | 3 | 3 |
| | | Glycerin | 3 | 3 | 3 |
| | Dye | Dihydroxyacetone | 5 | 5 | 5 |
| | Stabilizer | Sodium pyrosulfite | 0.02 | 0.02 | 0.02 |
| | Salting-out agent | Sodium chloride | 1 | 1 | 1 |

TABLE 1-continued

| Classification | | Raw material | Example 1 | Example 2 | Example 3 |
|---|---|---|---|---|---|
| | Chelating agent | Edetate (EDTA-2Na•2H$_2$O) | 0.1 | 0.1 | 0.1 |
| | Preservative | Phenoxy ethanol | 0.3 | 0.3 | 0.3 |
| Oil phase | Thickener | Organophilic clay mineral *1 | — | — | 2 |
| | Emulsifier | Cross-linked polyether-modified silicone *2 | 2.3 | 2 | — |
| | | Branched polyether-modified silicone *3 | 1 | — | 3 |
| | | Branched alkyl polyether-modified silicone *4 | — | 1 | — |
| | Oil components | Decamethylcyclopentasiloxane | 12.2 | 9 | 12.2 |
| | | Olefin oligomer *15 | 2 | — | 2 |
| | | Diisopropyl sebacate | 3 | — | — |
| | | Isononyl isononanoate | — | 2 | 3 |
| | | Octylmethoxy cinnamate | — | 5 | — |
| | | Octocrylene | — | 3 | — |
| | | Vitamin E acetate (V-E acetate) | — | — | 0.05 |
| | Coloring agent | Iron oxide (red): Silica coated + hydrophobed *5 | 0.4 | 0.4 | 0.4 |
| | | Iron oxide (yellow): Silica coated + hydrophobed *6 | 1 | 1 | 1 |
| | | Iron oxide (black): Silica coated + hydrophobed *7 | 0.5 | 0.5 | 0.5 |
| | | Iron oxide (red): Hydrophobed *8 | — | — | — |
| | | Iron oxide (yellow): Hydrophobed *9 | — | — | — |
| | | Iron oxide (red): Hydrophobed *10 | — | — | — |
| | | Iron oxide (yellow): Hydrophobed *11 | — | — | — |
| | | Iron oxide (black): Hydrophobed *12 | — | — | — |
| | Pearl agent | Dimeticone-treated titanium oxide-coated mica *13 | — | 0.7 | 0.7 |
| | Constitutional pigment | Alkyl-modified silicone resin-coated talc *14 | 2.1 | 1.4 | 1.4 |
| | | Total | 100 | 100 | 100 |
| Evaluation items | | Appearance and odor stability | ○ | ○ | ○ |
| | | Viscosity stability | ○ | ○ | ○ |
| | | Decorative effect on the skin | ○ | ○ | ○ |
| | | Sustained dyeing effect | ○ | ○ | ○ |

*1: Benton 38VCG (Elementis Specialties)
*2: KSG210 (Shin-Etsu Chemical Co., Ltd.)
*3: KF6028 (Shin-Etsu Chemical Co., Ltd.)
*4: KF6038 (Shin-Etsu Chemical Co., Ltd.)
*5: Powder prepared by treating the surface of CONCELIGHT RP-10S (from Catalyst & Chemicals Industries Co. Ltd.) with octyltriethoxysilane.
*6: Powder prepared by treating the surface of CONCELIGHT YP-10S (from Catalyst & Chemicals Industries Co. Ltd.) with octyltriethoxysilane.
*7: Powder prepared by hydrophobing the surface of CONCELIGHT BP-10S (from Catalyst & Chemicals Industries Co. Ltd.) with meticone and tetradecene.
*8: Powder prepared by treating the surface of red iron oxide with meticone and tetradecene.
*9: Powder prepared by treating the surface of yellow iron oxide with meticone and tetradecene.
*10: Powder prepared by treating the surface of red iron oxide with 1,3,5,7-tetraemethylcyclo-tetrasiloxane and tetradecene.
*11: Powder prepared by treating the surface of yellow iron oxide with 1,3,5,7-tetraemethylcyclo-tetrasiloxane and tetradecene.
*12: Powder prepared by treating the surface of black iron oxide with 1,3,5,7-tetraemethylcyclo-tetrasiloxane and tetradecene.
*13: Miyoshi Kasei Co. Ltd. Product name: SA-TIMICA GOLDENBRONZE
*14: Powder prepared by treating the surface of talc with 1,3,5,7-tetraemethylcyclo-tetrasiloxane and tetradecene.
*15: Nikko Chemicals Co. Product name: Syncelane 4

TABLE 2

| Classification | | Raw material | Example 4 | Example 5 | Comparative example 1 | Comparative example 2 |
|---|---|---|---|---|---|---|
| Water phase | Water | Ion-exchanged water | 62.88 | 43.08 | 63.03 | 33.08 |
| | Alcohol | Ethyl alcohol (95%) | 5 | 5 | 5 | 5 |
| | Humectant | Dipropylene glycol | 3 | 3 | 3 | 3 |
| | | Glycerin | 3 | 3 | 3 | 3 |
| | Dye | Dihydroxyacetone | 0.2 | 20 | 0.05 | 30 |
| | Stabilizer | Sodium pyrosulfite | 0.02 | 0.02 | 0.02 | 0.02 |
| | Salting-out agent | Sodium chloride | 1 | 1 | 1 | 1 |
| | Chelating agent | Edetate (EDTA-2Na•2H$_2$O) | 0.1 | 0.1 | 0.1 | 0.1 |
| | Preservative | Phenoxy ethanol | 0.3 | 0.3 | 0.3 | 0.3 |
| Oil phase | Thickener | Organophilic clay mineral *1 | — | — | — | — |
| | Emulsifier | Cross-linked polyether-modified silicone *2 | 2.3 | 2.3 | 2.3 | 2.3 |
| | | Branched polyether-modified silicone *3 | 1 | 1 | 1 | 1 |
| | | Branched alkyl polyether-modified silicone *4 | — | — | — | — |
| | Oil components | Decamethylcyclopentasiloxane | 12.2 | 12.2 | 12.2 | 12.2 |
| | | Olefin oligomer *15 | 2 | 2 | 2 | 2 |
| | | Diisopropyl sebacate | 3 | 3 | 3 | 3 |
| | | Isononyl isononanoate | — | — | — | — |
| | | Octylmethoxy cinnamate | — | — | — | — |
| | | Octocrylene | — | — | — | — |
| | | Vitamin E acetate (V-E acetate) | — | — | — | — |

TABLE 2-continued

| Classification | | Raw material | Example 4 | Example 5 | Comparative example 1 | Comparative example 2 |
|---|---|---|---|---|---|---|
| | Coloring agent | Iron oxide (red): Silica coated + hydrophobed *5 | 0.4 | 0.4 | 0.4 | 0.4 |
| | | Iron oxide (yellow): Silica coated + hydrophobed *6 | 1 | 1 | 1 | 1 |
| | | Iron oxide (black): Silica coated + hydrophobed *7 | 0.5 | 0.5 | 0.5 | 0.5 |
| | | Iron oxide (red): Hydrophobed *8 | — | — | — | — |
| | | Iron oxide (yellow): Hydrophobed *9 | — | — | — | — |
| | | Iron oxide (red): Hydrophobed *10 | — | — | — | — |
| | | Iron oxide (yellow): Hydrophobed *11 | — | — | — | — |
| | | Iron oxide (black): Hydrophobed *12 | — | — | — | — |
| | Pearl agent | Dimeticone-treated titanium oxide-coated mica *13 | — | — | — | — |
| | Constitutional pigment | Alkyl-modified silicone resin-coated talc *14 | 2.1 | 2.1 | 2.1 | 2.1 |
| | | Total | 100 | 100 | 100 | 100 |
| Evaluation items | Appearance and odor stability | | ○ | Δ | ○ | x |
| | Viscosity stability | | ○ | ○ | ○ | ○ |
| | Decorative effect on the skin | | ○ | ○ | ○ | ○ |
| | Sustained dyeing effect | | Δ | ○ | x | ○ |

*1-*17: Same as Table 1.

TABLE 3

| Classification | | Raw material | Example 6 | Comparative example 3 | Example 7 | Example 8 | Comparative example 4 | Comparative example 5 |
|---|---|---|---|---|---|---|---|---|
| Water phase | Water | Ion-exchanged water | 61.28 | 61.33 | 59.89 | 49.98 | 59.971 | 47.98 |
| | Alcohol | Ethyl alcohol (95%) | 5 | 5 | 5 | 5 | 5 | 5 |
| | Humectant | Dipropylene glycol | 3 | 3 | 3 | 3 | 3 | 3 |
| | | Glycerin | 3 | 3 | 3 | 3 | 3 | 3 |
| | Dye | Dihydroxyacetone | 5 | 5 | 5 | 5 | 5 | 5 |
| | Stabilizer | Sodium pyrosulfite | 0.02 | 0.02 | 0.02 | 0.02 | 0.02 | 0.02 |
| | Salting-out agent | Sodium chloride | 1 | 1 | 1 | 1 | 1 | 1 |
| | Chelating agent | Edetate (EDTA-2Na•2H$_2$O) | 0.1 | 0.1 | 0.1 | 0.1 | 0.1 | 0.1 |
| | Preservative | Phenoxy ethanol | 0.3 | 0.3 | 0.3 | 0.3 | 0.3 | 0.3 |
| Oil phase | Thickener | Organophilic clay mineral *1 | — | — | — | — | — | — |
| | Emulsifier | Cross-linked polyether-modified silicone *2 | — | — | 2.3 | 2.3 | 2.3 | 2.3 |
| | | Branched polyether-modified silicone *3 | 0.1 | 0.05 | 1 | 1 | 1 | 1 |
| | | Branched alkyl polyether-modified silicone *4 | — | — | — | — | — | — |
| | Oil components | Decamethylcyclopentasiloxane | 12.2 | 12.2 | 12.2 | 12.2 | 12.2 | 12.2 |
| | | Olefin oligomer *15 | 2 | 2 | 2 | 2 | 2 | 2 |
| | | Diisopropyl sebacate | 3 | 3 | 3 | 3 | 3 | 3 |
| | | Isononyl isononanoate | — | — | — | — | — | — |
| | | Octylmethoxy cinnamate | — | — | — | — | — | — |
| | | Octocrylene | — | — | — | — | — | — |
| | | Vitamin E acetate (V-E acetate) | — | — | — | — | — | — |
| | Coloring agent | Iron oxide (red): Silica coated + hydrophobed *5 | 0.4 | 0.4 | 0.01 | 2 | 0.001 | 3 |
| | | Iron oxide (yellow): Silica coated + hydrophobed *6 | 1 | 1 | 0.05 | 5.5 | 0.005 | 6 |
| | | Iron oxide (black): Silica coated + hydrophobed *7 | 0.5 | 0.5 | 0.03 | 2.5 | 0.003 | 3 |
| | | Iron oxide (red): Hydrophobed *8 | — | — | — | — | — | — |
| | | Iron oxide (yellow): Hydrophobed *9 | — | — | — | — | — | — |
| | | Iron oxide (red): Hydrophobed *10 | — | — | — | — | — | — |
| | | Iron oxide (yellow): Hydrophobed *11 | — | — | — | — | — | — |
| | | Iron oxide (black): Hydrophobed *12 | — | — | — | — | — | — |
| | Pearl agent | Dimeticone-treated titanium oxide-coated mica *13 | — | — | — | — | — | — |
| | Constitutional pigment | Alkyl-modified silicone resin-coated talc *14 | 2.1 | 2.1 | 2.1 | 2.1 | 2.1 | 2.1 |
| | | Total | 100 | 100 | 100 | 100 | 100 | 100 |
| Evaluation items | Appearance and odor stability | | ○ | ○ | ○ | Δ | ○ | x |
| | Viscosity stability | | Δ | x | ○ | Δ | ○ | x |
| | Decorative effect on the skin | | ○ | ○ | Δ | ○ | x | ○ |
| | Sustained dyeing effect | | ○ | ○ | ○ | ○ | ○ | ○ |

*1-*17: Same as Table 1.

TABLE 4

| Classification | Raw material | | Comparative example 6 | Comparative example 7 | Comparative example 8 | Comparative example 9 | Comparative example 10 |
|---|---|---|---|---|---|---|---|
| Water phase | Water | Ion-exchanged water | 58.08 | 58.08 | 58.08 | 58.08 | 58.08 |
| | Alcohol | Ethyl alcohol (95%) | 5 | 5 | 5 | 5 | 5 |
| | Humectant | Dipropylene glycol | 3 | 3 | 3 | 3 | 3 |
| | | Glycerin | 3 | 3 | 3 | 3 | 3 |
| | Dye | Dihydroxyacetone | 5 | 5 | 5 | 5 | 5 |
| | Stabilizer | Sodium pyrosulfite | 0.02 | 0.02 | 0.02 | 0.02 | 0.02 |
| | Salting-out agent | Sodium chloride | 1 | 1 | 1 | 1 | 1 |
| | Chelating agent | Edetate (EDTA-2Na•2H$_2$O) | 0.1 | 0.1 | 0.1 | 0.1 | 0.1 |
| | Preservative | Phenoxy ethanol | 0.3 | 0.3 | 0.3 | 0.3 | 0.3 |
| Oil phase | Thickener | organophilic clay mineral *1 | — | — | — | — | — |
| | Emulsifier | Cross-linked polyether-modified silicone *2 | 2.3 | 2.3 | 2.3 | 2.3 | 2.3 |
| | | Branched polyether-modified silicone *3 | 1 | 1 | 1 | 1 | 1 |
| | | Branched alkyl polyether-modified silicone *4 | — | — | — | — | — |
| | Oil components | Decamethylcyclopentasiloxane | 12.2 | 12.2 | 12.2 | 12.2 | 12.2 |
| | | Olefin oligomer *15 | 2 | 2 | 2 | 2 | 2 |
| | | Diisopropyl sebacate | 3 | 3 | 3 | 3 | 3 |
| | | Isononyl isononanoate | — | — | — | — | — |
| | | Octylmethoxy cinnamate | — | — | — | — | — |
| | | Octocrylene | — | — | — | — | — |
| | | Vitamin E acetate (V-E acetate) | — | — | — | — | — |
| | Coloring agent | Iron oxide (red): Silica coated + hydrophobed *5 | — | 0.4 | — | 0.4 | 0.4 |
| | | Iron oxide (yellow): Silica coated + hydrophobed *6 | 1 | — | 1 | — | 1 |
| | | Iron oxide (black): Silica coated + hydrophobed *7 | 0.5 | 0.5 | 0.5 | 0.5 | — |
| | | Iron oxide (red): Hydrophobed *8 | 0.4 | — | — | — | — |
| | | Iron oxide (yellow): Hydrophobed *9 | — | 1 | — | — | — |
| | | Iron oxide (red): Hydrophobed *10 | — | — | 0.4 | — | — |
| | | Iron oxide (yellow): Hydrophobed *11 | — | — | — | 1 | — |
| | | Iron oxide (black): Hydrophobed *12 | — | — | — | — | 0.5 |
| | Pearl agent | Dimeticone-treated titanium oxide-coated mica *13 | — | — | — | — | — |
| | Constitutional pigment | Alkyl-modified silicone resin-coated talc *14 | 2.1 | 2.1 | 2.1 | 2.1 | 2.1 |
| | | Total | 100 | 100 | 100 | 100 | 100 |
| Evaluation items | Appearance and odor stability | | x | x | x | x | x |
| | Viscosity stability | | x | x | x | x | x |
| | Decorative effect on the skin | | ○ | ○ | ○ | ○ | ○ |
| | Sustained dyeing effect | | ○ | ○ | ○ | ○ | ○ |

*1-*17: Same as Table 1.

INDUSTRIAL APPLICABILITY

The self tanning cosmetic of the present invention is a cosmetic used to give a suntan color to the skin without exposure to sunlight (ultraviolet light); it is a tint type self tanning cosmetic having an instantaneous coloring effect (decorative effect) and a long term coloring effect.

Since an inorganic pigment can be added in a stable manner, it can also be used as a makeup cosmetic having a self tanning effect.

The invention claimed is:

1. A water-in-oil type emulsified self tanning cosmetic containing:
   0.2-20.0 mass % of dihydroxyacetone,
   0.1-10.0 mass % of silica-coated iron oxide powder having a hydrophobed surface, the silica coating comprising 1-30 mass % of the silica-coated iron oxide powder,
   0.1-10.0 mass % of one or more emulsifiers comprised of branched polyether modified silicone and/or cross-linked polyether-modified silicone, and
   wherein a mass ratio of the oil phase and water phase (oil phase/water phase) is 6/4-1/9.

2. The water-in-oil type emulsified self tanning cosmetic of claim 1, wherein said iron oxide powder is hydrophobically treated with octyltriethoxysilane.

3. The water-in-oil type emulsified self tanning cosmetic of claim 1, wherein the silica coating comprises 2-20 mass % of the silica-coated iron oxide pigment.

4. The water-in-oil type emulsified self tanning cosmetic of claim 1, further comprising one or more of powder ingredients, liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, ultraviolet absorbents, sequestering agents, lower alcohols, polyhydric alcohols, sugars, amino acids, organic amines, polymer emulsions, pH adjusting agents, skin nutrients, vitamins, antioxidants, antioxidation assistants, perfumes, and water.

5. The water-in-oil type emulsified self tanning cosmetic of claim 1, wherein a mass ratio of the oil phase and the water phase (oil phase/water phase) is 4/6-2/8.

6. The water-in-oil type emulsified self tanning cosmetic of claim 1, wherein a mass ratio of the oil phase and the water phase (oil phase/water phase) is 3/7.

7. A water-in-oil type emulsified self tanning cosmetic comprising:
- 3-10 mass % of dihydroxyacetone,
- 1-5 mass % of silica-coated iron oxide powder having a surface hydrophobed with octyltriethoxysilane, the silica coating comprising 1-30 mass % of the silica-coated iron oxide powder,
- 0.1-10.0 mass % of emulsifiers, the emulsifiers comprising branched polyether-modified silicone and/or cross-linked polyether-modified silicone,
- 50-85 mass % of water,
- 15-20 mass % of an oil component,
- 1-10 mass % of a polyol, and
- wherein a mass ratio of the oil phase and water phase (oil phase/water phase) is 6/4-1/9.

8. A water-in-oil type emulsified self tanning cosmetic comprising:
- 5.0 mass % of dihydroxyacetone,
- 1.9 mass % of silica-coated iron oxide powder having a surface hydrophobed with octyltriethoxysilane, the silica coating comprising 1-30 mass % of the silica-coated iron oxide powder,
- 3.0-3.3 mass % of emulsifiers, the emulsifiers comprising branched polyether-modified silicone and/or cross-linked polyether-modified silicone, and
- wherein a mass ratio of the oil phase and water phase (oil phase/water phase) is 6/4-1/9.

* * * * *